United States Patent
DeBoer et al.

(10) Patent No.: US 9,427,312 B2
(45) Date of Patent: Aug. 30, 2016

(54) ACCOMMODATING INTRAOCULAR COMPOSITE LENS AND RELATED METHODS

(71) Applicants: Charles DeBoer, Pasadena, CA (US); Yu-Chong Tai, Pasadena, CA (US); Mark S. Humayun, Glendale, CA (US)

(72) Inventors: Charles DeBoer, Pasadena, CA (US); Yu-Chong Tai, Pasadena, CA (US); Mark S. Humayun, Glendale, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 49 days.

(21) Appl. No.: 13/896,539

(22) Filed: May 17, 2013

(65) Prior Publication Data

US 2013/0317607 A1 Nov. 28, 2013

Related U.S. Application Data (60) Provisional application No. 61/651,694, filed on May 25, 2012.

(51) Int. Cl.
*A61F 2/16* (2006.01)

(52) U.S. Cl.
CPC ........... *A61F 2/1613* (2013.01); *A61F 2/1624* (2013.01); *A61F 2/1635* (2013.01); *A61F 2/1648* (2013.01); *A61F 2/1616* (2013.01); *A61F 2/1629* (2013.01)

(58) Field of Classification Search
CPC ............. A61F 2/1613–2/1629; A61F 2/1635; A61F 2/1637; A61F 2/1648
See application file for complete search history.

(56) References Cited

U.S. PATENT DOCUMENTS

| | | | |
|---|---|---|---|
| 4,822,360 A | 4/1989 | Deacon | |
| 4,883,485 A | 11/1989 | Patel | |
| 4,902,293 A | 2/1990 | Feaster | |
| 5,554,187 A | 9/1996 | Rizzo, III | |
| 6,730,123 B1 | 5/2004 | Klopotek | |
| 7,438,723 B2 | 10/2008 | Esch | |
| 8,029,136 B2 | 10/2011 | Dick et al. | |
| 8,038,711 B2 | 10/2011 | Clarke | |
| 8,447,086 B2 | 5/2013 | Hildebrand et al. | |
| 8,603,164 B2 | 12/2013 | Peyman | |
| 2001/0049532 A1 | 12/2001 | Saishin et al. | |
| 2002/0161344 A1 | 10/2002 | Peclat et al. | |
| 2003/0083744 A1 | 5/2003 | Khoury | |
| 2004/0111153 A1* | 6/2004 | Woods .................. | A61F 2/1613 623/6.37 |
| 2004/0169816 A1* | 9/2004 | Esch ........................ | 351/160 R |

(Continued)

FOREIGN PATENT DOCUMENTS

| | | | |
|---|---|---|---|
| EP | 1958592 A1 | 8/2008 | |
| EP | 2221024 A1 | 8/2010 | |

(Continued)

OTHER PUBLICATIONS

International Application No. PCT/US2012/038102, International Search Report and Written Opinion mailed on Nov. 30, 2012, 17 pages.

(Continued)

*Primary Examiner* — Howie Matthews
(74) *Attorney, Agent, or Firm* — Morgan, Lewis & Bockius LLP (57) ABSTRACT

An implantable intraocular lens and methods of manufacturing them provide a target degree of optical accommodation. In various embodiments, the lens includes at least one internal optic, an outer shell for enclosing at least a portion of the internal optic, and a fluid at least partially filling the outer shell.

18 Claims, 7 Drawing Sheets

(56) References Cited

U.S. PATENT DOCUMENTS

| | | |
|---|---|---|
| 2004/0190153 A1 | 9/2004 | Esch |
| 2006/0047339 A1 | 3/2006 | Brown |
| 2007/0129800 A1 | 6/2007 | Cumming |
| 2007/0142909 A1 | 6/2007 | Peyman |
| 2008/0114372 A1 | 5/2008 | Edwards et al. |
| 2008/0319451 A1 | 12/2008 | Zacharias |
| 2009/0043384 A1* | 2/2009 | Niwa et al. ............ 623/6.13 |
| 2009/0240208 A1 | 9/2009 | Cowan et al. |
| 2011/0270596 A1 | 11/2011 | Weeber |
| 2012/0116506 A1 | 5/2012 | Compertore |
| 2012/0296423 A1 | 11/2012 | Caffey et al. |
| 2013/0304203 A1 | 11/2013 | Beer |
| 2014/0111765 A1 | 4/2014 | DeBoer et al. |

FOREIGN PATENT DOCUMENTS

| | | |
|---|---|---|
| GB | 1481427 A | 7/1977 |
| WO | 92/17132 A1 | 10/1992 |
| WO | 2004/054471 A2 | 7/2004 |
| WO | WO-2004085571 A1 | 10/2004 |
| WO | 2010/035139 A2 | 4/2010 |
| WO | WO-2012067994 A2 | 5/2012 |
| WO | 2014/063135 A2 | 4/2014 |
| WO | 2014/063135 A3 | 8/2014 |

OTHER PUBLICATIONS

PCT International Application No. PCT/US2013/065858, International Search Report and Written Opinion mailed Jul. 2, 2014, 10 pages.

PCT International Application No. PCT/US2012/038102, International Preliminary Report on Patentability mailed Nov. 28, 2013, 13 pages.

International Search Report and Written Opinion mailed Apr. 19, 2013 for International Application No. PCT/US2013/041545 (10 pages).

* cited by examiner

ACCOMMODATING INTRAOCULAR COMPOSITE LENS AND RELATED METHODS

CROSS-REFERENCE TO RELATED APPLICATIONS

This application claims priority to and the benefit of, and incorporates herein by reference in its entirety, U.S. Provisional Patent Application No. 61/651,694, which was filed on May 25, 2012.

FIELD OF THE INVENTION

In various embodiments, the present invention relates generally to implantable intraocular lenses and, more specifically, to an accommodating intraocular lenses implanted in a patient's eye.

BACKGROUND

The crystalline lens of a human's eye refracts and focuses light onto the retina. Normally the lens is clear, but it can become opaque (i.e., when developing a cataract) due to aging, trauma, inflammation, metabolic or nutritional disorders, or radiation. While some lens opacities are small and require no treatment, others may be large enough to block significant fractions of light and obstruct vision.

Conventionally, treatments to the cataract involve surgically removing the opaque lens matrix from the lens capsule using, for example, phacoemulsification and/or a femtosecond laser through a small incision in the periphery of the patient's cornea. An artificial intraocular lens (IOL) can then be implanted in a lens capsule bag (the so-called "in-the-bag implantation") to replace the crystalline lens. Generally, IOLs are made of a foldable material, such as silicone or acrylics, for minimizing the incision size and required stitches and, as a result, the patient's recovery time. The most commonly used IOLs are single-element lenses (or monofocal IOLs) that provide a single focal distance; the selected focal length typically affords fairly good distance vision. However, because the focal distance is not adjustable following implantation of the IOL, patients implanted with monofocal IOLs can no longer focus on objects at a close distance (e.g., less than twenty-five centimeters); this results in poor visual acuity at close distances. To negate this disadvantage, multifocal IOLs are used to provide dual foci at both near and far distances. However, due to the optical design of such lenses, patients implanted with multifocal IOLs suffer from a loss of vision sharpness (e.g., blurred vision). In addition, patients may experience visual disturbances, such as halos or glare, because of the simultaneous focus at two distances.

Recently, accommodating intraocular lenses (AIOLs) have been developed to provide adjustable focal distances (or accommodations) relying on the natural focusing ability of the eye (e.g., using contractions of ciliary muscles). Conventional AIOLs include, for example, a single optic that translates its position along the visual axis of the eye, dual optics that change the distance between two lenses, and curvature-changing lenses that change their curvatures to adjust the focus power. These designs, however, tend to be too complex to be practical to construct and/or have achieved limited success (e.g., providing a focusing power of only 1-2 diopters).

Additionally, IOL implantations may cause post-surgical complications. For example, when the crystalline lens is removed through a small incision in the anterior part of the lens capsule, the posterior side of the capsule is left intact to prevent vitreous humor from entering the anterior chamber of the eye. The intact posterior lens capsules, however, may develop haziness of the capsule, known as posterior capsular opacification (PCO), which results in blurry vision. This is due to the growth and migration of lens epithelial cells on the lens capsule, which frequently remain present following cataract surgery and represent one of the most common post-surgical complications of IOL implantation. Although a neodymium-doped yttrium aluminium garnet (Nd:YAG) laser may be utilized to open an aperture in the posterior lens capsule to remove the opacity of the capsule, and thereby restore vision, this treatment requires an extra procedure and poses an additional risk of damaging the implanted IOLs.

Consequently, there is a need for IOLs that provide a high degree of accommodation and appropriate focusing power, and which can be easily manufactured and implanted in human eyes. In addition, it is desirable for surgical complications, such as PCO, to be avoided after IOL implantation.

SUMMARY

In various embodiments, the present invention relates to an AIOL including an outer IOL shell, at least one internal optic enclosed therein, and a medium in the space between the internal optic and IOL shell to increase the accommodation and generate an appropriate focusing power. More specifically, the accommodation of the AIOL can be effectively altered or customized by varying the shape of the outer IOL shell, the shape and refractive index of the internal lens, and the volume and refractive index of the filling medium. In various embodiments, the shape of the outer IOL shell is identical for all AIOLs in order to reduce the manufacturing cost, while the properties of the internal optic and filling medium are varied to adjust the accommodation and focusing power to suit a particular patient. In addition, the shape of the outer IOL shell may be designed to accommodate the geometry of the eye (e.g., to fit within the lens capsule), thereby providing implantation comfort to the patients. Further, the surface of the AIOL may be modified to eliminate the growth and migration of lens epithelial cells on the lens capsule, thereby avoiding post-surgical complications. In one embodiment, the outer shell, the internal optic 204, and/or the filling medium include blue-light-absorbing chromophores for blocking UV radiation, thereby protecting the retina.

In some embodiments, the internal optic is a diverging optic that reduces the optical power attributable to the outer IOL shell. As a result, the accommodation of the AIOL may be beneficially increased by the outer IOL shell while the focusing power thereof is reduced to an appropriate level. In one implementation, more than one internal optic is incorporated in the AIOL; this further improves accommodation by dynamically adjusting the properties (e.g., refractive index) of each internal optic and the distances therebetween. In addition, the internal optic(s) may be integrated with the wall of the outer IOL shell to increase the thickness of the AIOL at the integrated portion(s); the thicker wall may resist the friction occurring during the AIOL insertion, thereby reducing damage to the thin portions of the AIOL walls. Because the AIOL may include two internal optics integrated with the anterior and posterior surfaces of the AIOL (resulting in thick portions on both anterior and posterior walls), the AIOL may be easily implanted into the eye via an aperture on either side of the anterior or posterior lens capsule.

As used herein, the term "accommodation" refers both to the eye's ability to change its optical power to focus on an object at various distances and to the capacity of a lens in accordance herewith to change its optical properties in response to the eye's accommodation mechanism. In addition, the terms "optical power," "focusing power," "lens power," and "refractive power" are used herein interchangeably.

Accordingly, in one aspect, the invention pertains to an implantable intraocular lens including an outer shell, one or more internal optics at least partially within the outer shell, and a first fluid at least partially filling the outer shell. In various embodiments, the refractive index of the first fluid, the degree of filling of the outer shell with the first fluid, the curvature of the outer shell, the axial position of the internal optic(s), and the curvature of the internal optic(s) cooperate to define the accommodation and refractive power of the lens. In one embodiment, the first fluid is a pharmacological agent.

The internal optic(s) may be integrated with the outer shell. The internal optic(s) may be or include a diverging lens. In various embodiments, the internal optic(s) are made of a solid material and/or include a second shell at least partially filled with a second fluid; in the latter case, the first and second fluids exhibit mutual repulsion therebetween. In one implementation, the internal optic(s) include one or more valves thereon for selective passage therethrough of the second fluid. The first and second fluids may have different refractive indices.

In various embodiments, the internal optic(s) are fully within the outer shell, which further includes a septum for supporting the internal optic(s) therewithin. In one implementation, the septum includes one or more apertures for allowing fluidic communication between different compartments within the outer shell formed by the septum. In one embodiment, the internal optic(s) consist of two optics which are integrated with opposed inner surfaces of the outer shell; a change in relative position between the optics alters the accommodation.

In some embodiments, the outer shell includes one or more valves thereon for selective passage of the first fluid through the outer shell. The outer shell may be shaped to conform to the geometry of the eye. The refractive index of the first fluid may be different from that of the aqueous humor. In one embodiment, the outer surface of the outer shell includes a feature creating a discontinuity thereon. In another embodiment, the outer surface of the outer shell includes an adhesive. In still another embodiment, the outer surface of the outer shell is modified with functional groups to prevent proliferation or migration of lens epithelial cells.

In another aspect, the invention relates to a method of manufacturing an implantable intraocular lens with a target accommodation level and a target refractive power. In various embodiments, the method includes providing an outer shell conforming to the geometry of the eye; at least partially enclosing one or more internal optics in the outer shell; and injecting a selected volume of a first fluid into the outer shell. In one implementation, the selected volume of the first fluid, the refractive index of the first fluid, the curvature of the outer shell, the axial position of the internal optic, and the curvature of the internal optic cooperate to provide the target accommodation level and refractive power.

The method may further include integrating the internal optic(s) with the outer shell. In addition, the method may include injecting a pharmacological agent into the outer shell. In such embodiments, the pharmacological agent is released or diffuses out of the implantable intraocular lens in a controlled manner.

In various embodiments, the method includes injecting a selected volume of a second fluid into the internal optic(s), in which case the target refractive power is determined also by the selected volume and the refractive index of the second fluid. The first fluid and second fluid may have different refractive indices.

In one embodiment, the method includes providing a feature creating a discontinuity on an outer surface of the outer shell. In another embodiment, the method includes providing an adhesive to the outer surface of the outer shell. In still another embodiment, the method includes modifying the outer surface of the outer shell to prevent proliferation or migration of lens epithelial cells.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, routines, steps, or characteristics may be combined in any suitable manner in one or more examples of the technology. The terms "substantially" and "approximately" mean ±10% and, in some embodiments, within ±5%. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
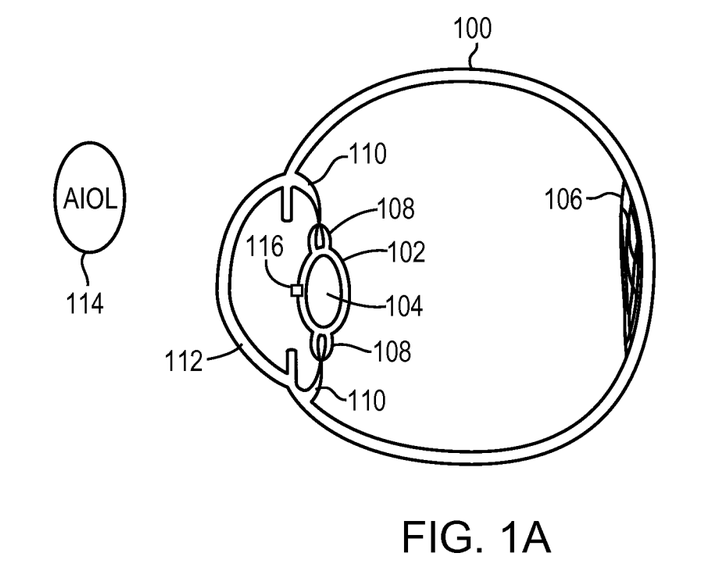
FIGS. 1A and 1B depict sectional side views, respectively, of a human eye and an AIOL in accordance with an embodiment of the invention.
Figure 1B:
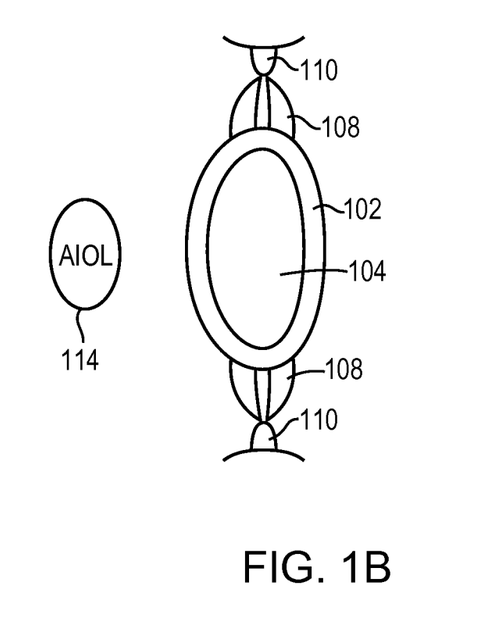

Refer first to FIGS. 1A and 1B, which illustrate a structure and operation of a human eye 100. The eye 100 has a lens capsule 102 with a crystalline lens 104 that focuses light onto the retina 106; the lens capsule 102 is joined by ligament fibers 108 around its circumference to ciliary muscles 110, which are further attached to the inner surface of the eye 100. In various embodiments of the present invention, during cataract surgery, lens 104 is removed from the lens capsule 102 using, for example, phacoemulsification and/or a femtosecond laser through a small incision in the periphery of the patient's cornea 112. An AIOL 114 as further described below is inserted through a small incision on the anterior capsule portion 116 into the lens capsule 102. The surgeon then ensures that the AIOL 114 is deployed and placed correctly and that there are no tears in the capsule 102.

Figure 2A:
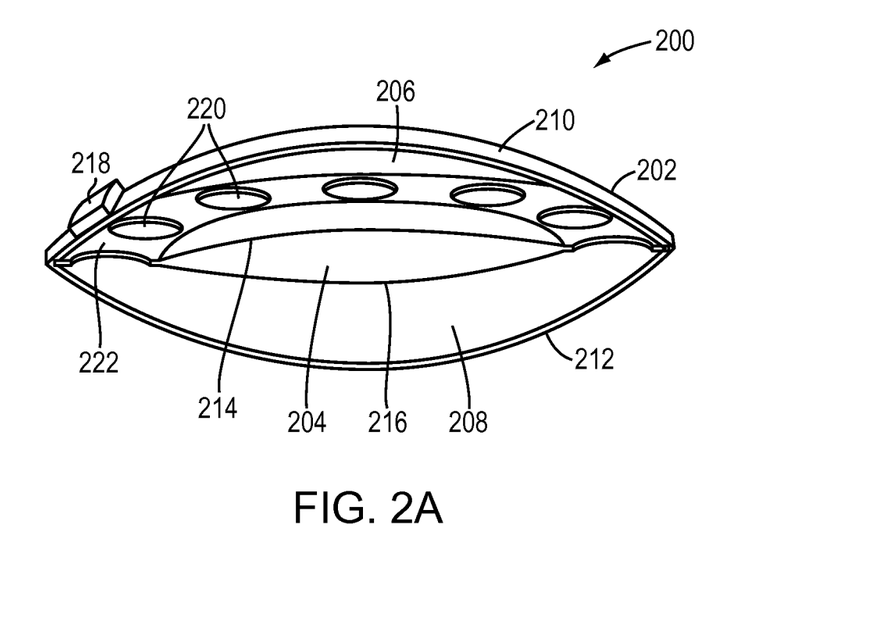
FIGS. 2A and 2B schematically depict an AIOL in accordance with an embodiment of the invention.

Referring to FIG. 2A, in various embodiments, the AIOL 200 includes an outer intraocular lens 202 enclosing an internal optic 204, a medium-filled anterior compartment 206 and a posterior compartment 208 created between the intraocular lens 202 and the internal optic 204. The internal optic 204 is not necessarily spherical and may be of any shape. Additionally, the internal optic 204 may be positioned at the equator of the AIOL 200 or at another location within the AIOL 200. The focusing power of the AIOL 200 may be varied by adjusting the shape (or curvature) of the outer IOL 202, the shape and/or refractive index of the internal optic 204, and/or the volume and/or refractive index of the filling medium.

During eye accommodation, ciliary muscles 110 release tension applied to the lens capsule 102, which results in a shape change of the lens capsule 102 and the AIOL 200 implanted therein. For example, the anterior surface 210 or posterior surface 212 of the AIOL 200 may undergo a change in curvature radius and/or move in the anterior or posterior direction. In one embodiment, the outer IOL 202 is molded in the same geometry (e.g., a one-size-fit-all outer IOL 202) to reduce manufacturing costs. The eye's accommodation level is controlled by the shape and refractive index of the internal optic 204 and/or the index of the medium filling the anterior compartment 206. For example, to satisfy patients having various focusing power requirements, the AIOLs 200 may be produced with identically shaped outer IOLs 202 while incorporating different internal optics 204 and/or different filling media therein to provide different focusing powers. In some embodiments, the shape of the outer IOL 202 is designed to conform to the geometry of the eye (e.g., fitting within the lens capsule 102); this ensures the patient's comfort and the achievement of good focusing power after the AIOL implantation. Alternatively, the outer IOL 202 may be manufactured in a few different sizes that all fit within a typical patient's lens capsule or may be customized for the lens capsules of particular patients. This approach may reduce the amount of additional correction required from the internal optic and/or filling medium. In some embodiments, the outer IOL 202, the internal optic 204, and/or the filling medium includes one or more ultraviolet A (UVA), ultraviolet B (UVB), and/or blue-light-absorbing chromophores for blocking UV radiation (e.g., up to 400 nm), thereby protecting the retina 106. Blue-light-absorbing chromophores are disclosed, for example, in U.S. Pat. Nos. 5,470,932 and 5,543,504, the entire disclosures of which are hereby incorporated by reference.

Figure 2B:
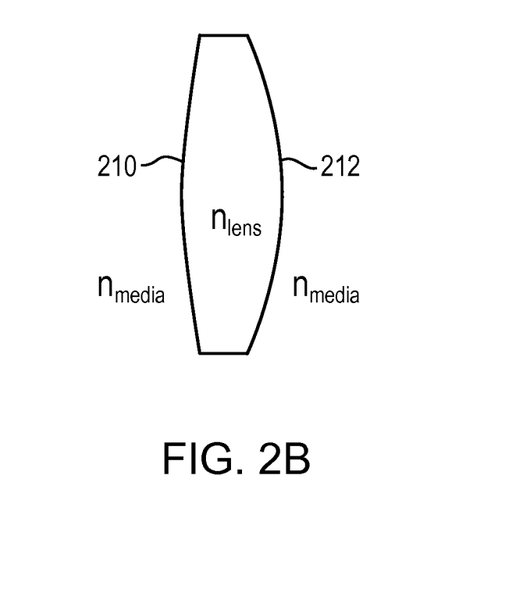

Referring to FIG. 2B, the optical power (which is typically defined as the inverse of focal length) of an AIOL having no internal optic 204 in a surrounding medium (e.g., aqueous humor) may be approximately computed using the lensmaker's formula for a thin lens:

$$\text{Power} = \frac{1}{f} = \frac{n_{lens} - n_{media}}{n_{media}} \left[ \frac{1}{R_1} - \frac{1}{R_2} \right], \quad \text{Eq. (1)}$$

where $n_{media}$ and $n_{lens}$ are the refractive indices of the surrounding medium and AIOL, respectively, and $R_1$ and $R_2$ are the curvatures of the anterior lens surface 210 and posterior lens surface 212 of the AIOL, respectively. If changes in the relative position of the anterior lens surface 210 and posterior lens surface 212 are negligible, the accommodation of the AIOL can be approximated as:

$$\text{Accom} = \frac{n_{lens} - n_{media}}{n_{media}} \left[ \frac{1}{\Delta R_1} - \frac{1}{\Delta R_2} \right]. \quad \text{Eq. (2)}$$

Eq. (2) indicates that once the refractive index of the AIOL has been determined, the accommodation of the AIOL 200 is adjustable by changing the radius of curvature of both the anterior surface 210 and/or the posterior surface 212 of outer shell 202. For example, the accommodation level may be increased by using an AIOL with a larger refractive index. For example, assuming $n_{media}$ is roughly 1.336, varying $n_{lens}$ from 1.4 to 1.47 results in a calculated increase in the accommodation level by a factor of approximately 2.1 (i.e., from 5 diopters to 10.5 diopters). This increase in accommodation comes at a cost, however: the overall power of the IOL increases, as indicated in Eq. (1). To address this, a diverging optic can be placed in the center as described below; an internal optic with a negative power compensates for the increase in overall power.

It should be noted that although the focusing power and accommodation are described herein using the thin lens formula, a thick lens formula can be used to predict increasing focusing power and accommodation level with an increased refractive index of the AIOL.

The filling medium may consist essentially of one or more refractive liquids, gels, curable polymers, or a compressible gas. In various embodiments, the AIOL 200 is implanted with compartments 206 and 208 unfilled; this enables the AIOL 200 to be easily rolled up for ease of introduction into the lens capsule 102 of an eye. After implantation, one or more media are introduced into the AIOL 200 via, for example, a refill valve 218. Upon injection, the filling medium flows from the anterior compartment 206 to the posterior compartment 208 via one or more apertures 220 on a septum 222 that supports the internal optic 204. In some embodiments, the medium is a pharmacological agent that can be released from or diffuses out of the AIOL 200 in a controlled manner (e.g., using a controller) and can be replenished using the valve 218. Accordingly, the implanted AIOL 200 may be a replacement of the crystalline lens and/or a drug pump delivering a therapeutic agent to the eye.

Figure 3A:
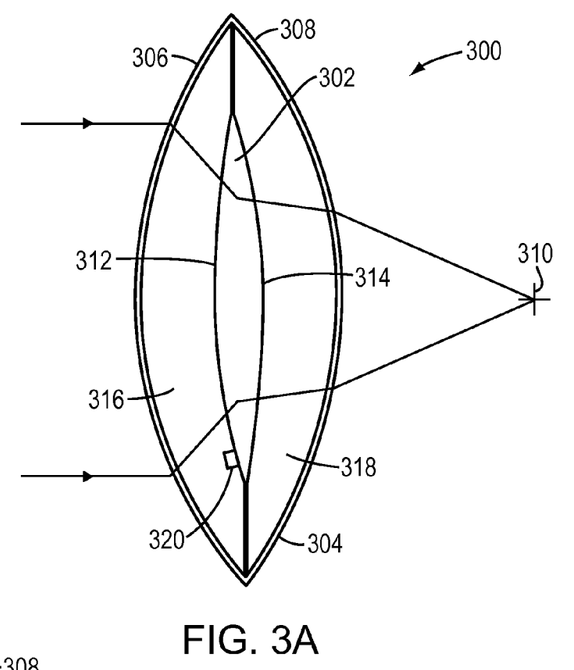
FIGS. 3A-3C schematically depict side views of various AIOLs in accordance with various embodiments of the invention.

Eqs. (1) and (2) indicate that increasing the accommodation level using a high-index AIOL (e.g., by increasing the refractive index of the filling medium) comes at the cost of a high optical power. In fact, by increasing the accommodation level by a factor of 2.1, the optical power is also approximately increased by a factor of 2.1. Referring to FIG. 3A, in various embodiments, the internal optic of the AIOL 300 includes a diverging lens 302 to reduce the overall optical power. Because the outer IOL 304 has a converging anterior lens surface 306 and a converging posterior lens surface 308 (thereby providing a positive focusing power), embedding a diverging lens, which has a negative focusing power, reduces the overall optical power of the AIOL 300. More specifically, when collimated light emitted from a light source first enters the AIOL 300, the light is refracted inward by the anterior lens surface 306 of the AIOL 300. The light is then refracted outward by the internal diverging lens 302, then by refraction inward at the posterior lens surface 308, ultimately focusing at a position 310. The diverging lens 302 may be a convex or concave lens as long as its refractive index is selected to create a negative focusing power based on the refractive index of the surrounding medium in the anterior and posterior compartments 316, 318. Accordingly, the AIOL 300 advantageously uses the diverging lens 302 to reduce focal power while providing a high accommodation level that may be adjusted by varying the curvatures of the anterior and posterior lens surfaces 306, 308 of the AIOL 300, the curvatures of the anterior and posterior surfaces 312, 314 of the internal optic 302, and the refractive index of the internal optic 302.

The internal optic 302, which may be used to adjust accommodation and focusing power for treating emmetropia, optical aberrations and astigmatism, may be made of a solid material, such as acrylic, silicone, PMMA, or parylene. Alternatively, the internal optic 302 may be filled with a fluid, in which case the refractive index thereof may be tuned by changing the volume and/or components of the fluid. In one embodiment, the fluid filling the internal optic 302 repels the medium filling the anterior and posterior compartments 316, 318; this prevents interdiffusion or exchange of the fluid and medium so that each separately maintains a constant refractive index. For example, the internal optic 302 may be filled with a hydrophilic liquid, such as sugar water, while the anterior compartment and posterior compartments 316, 318 are filled with a hydrophobic medium, such as silicone oil. As a result, the silicone oil prevents the water or sugar moieties from diffusing into the anterior compartment and posterior compartments 316, 318, and the sugar water prevents the silicone oil from diffusing into the internal optic 302. In some embodiments, the internal optic 302 includes a valve 320 to permit a fluid to be injected into the internal optic 302 prior to or after the AIOL implantation.

The internal optic 302 may be a separate component located within the outer IOL 304 as described above. Alternatively, with reference to FIG. 3B, the internal optic 302 may be integrated with the outer IOL 304; this creates a single internal chamber 322 that can be filled with a fluid medium. Again, the accommodation of the AIOL may be adjusted by changing the volume or refractive index of the filling medium. In one embodiment, the internal optic 302 is integrated with a portion of the outer IOL 302 along the optical axis 323 thereof. During accommodation, the shape of the optic 302 may remain unchanged while its position translates along the optical axis due to the shape change of the IOL surfaces 306, 308. The internal optic 302 may have any suitable shape and may have the same or a different refractive index from that of the IOL wall and/or the filling medium in the chamber 322. In order to suit the needs of various patients, the overall accommodation and focal power of AIOL embodiments having an internal optic 302 integrated with the outer IOL 304 may be adjusted by the shape of the IOL walls 306, 308, the position translation of the internal optic 302, and/or the refractive index and volume of the filling medium in the chamber 322.

Figure 3B:
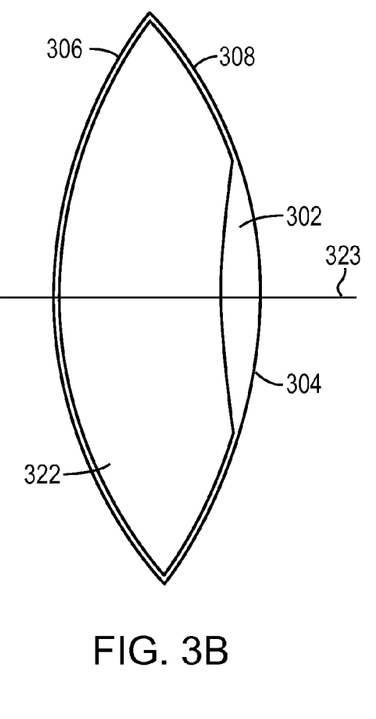

Because the thickness of the AIOL in the portion where the internal optic 302 is integrated is thicker and less flexible than other areas of the AIOL, the integrated inner optic 302 may advantageously prevent the AIOL from bulging across the capsular incision used to insert the AIOL or an incision in the posterior portion of the lens capsule. In addition, the AIOL may be rolled up with the thicker portion facing outwards; as a result, friction occurring during the AIOL insertion is exerted on the thicker portion. This reduces the risk of damaging the thin-walled areas of the AIOL during implantation.

Figure 3C:
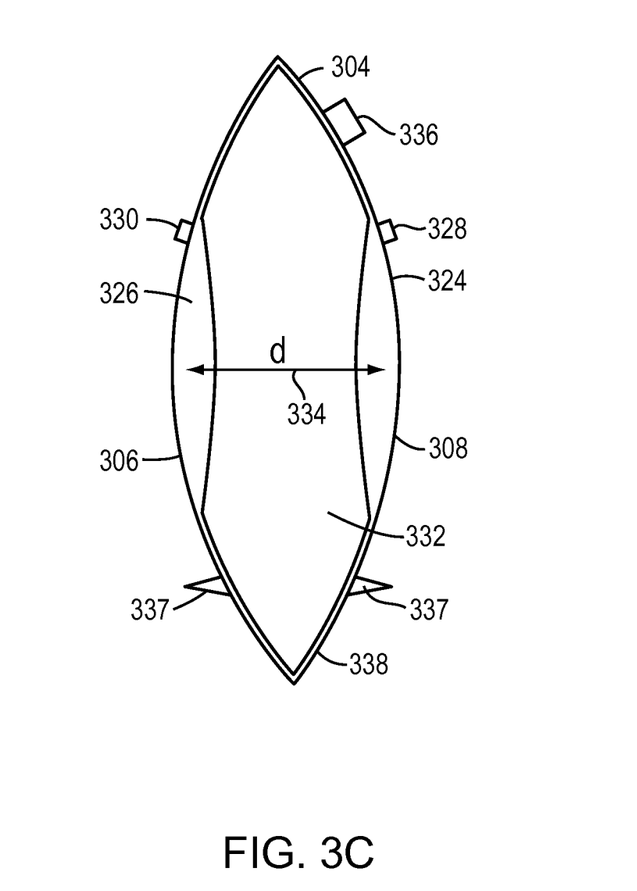

Referring to FIG. 3C, in various embodiments, the AIOL includes two internal optics 324, 326 that may be located anywhere inside the outer IOL 304. Again, the internal optics 324, 326 may be made of solid materials or filled with fluids through the refill valves 328, 330 thereon. Because each internal optic may be filled with fluid individually, its refractive index is independently variable, providing an additional adjustment for the optical power and accommodation of the AIOL. Therefore, the overall accommodation and/or focusing power of the AIOL may be adjusted by various factors, including the shape of the outer IOL 304, the shape of the internal optics 324, 326, the refractive indices of the fluids contained in the optics 324, 326, the refractive index of the medium in the chamber 332, and/or the axial distance 334 between the two optics 324, 326. In addition, this design advantageously allows the AIOL to be entirely or partially deflated during insertion and inflated following insertion (using, for example, refilling valves 328, 330, 336), thereby significantly reducing the incision size.

In one embodiment, the two internal optics 324, 326 are integrated with (i.e., form a part of) the anterior inner surface 306 and posterior surface 308 of the outer IOL 304, respectively; this AIOL may be suitable for a cap sulotomy procedure on either surface (i.e., anterior or posterior surface) of the lens capsule. Again, because the thickness of the AIOL in the portions where the internal optics 324, 326 are integrated is thicker and less flexible than other areas of the AIOL, the AIOL surfaces having the integrated inner optics 324, 326 may be used to withstand the brunt of the friction occurring during the AIOL insertion. Additionally, the thicker portion of the posterior surface 308 may reduce the risk of damaging the AIOL when a YAG capsulotomy is performed on the posterior lens capsule for treating the PCO complication.

To negate the post-surgical complications and thereby avoid the YAG capsulotomy, in one embodiment, the outer surface of the AIOL is modified with functional groups, such as hydroxyl, amine or amide, carboxylic acid, fluoro modified groups, alkyl groups, parylene, or implanted with pharmaceuticals (such as chemotherapy agents) to kill and/or prevent movement of lens epithelial cells. In another embodiment, the outer surface of the AIOL includes an angled circumferential edge 337 to create a discontinuity thereon and/or an adhesive member 338. The discontinuity 337 and/or adhesive layer 338 prevents lens epithelial cells from migrating and causing posterior capsular opacification (PCO) or anterior capsular opacification (ACO). In one embodiment, the circumferential edge 337 and/or adhesive layer 338 is placed outside the central optical zone (e.g., 3 mm away from the optical axis 323) of the AIOL. In addition, the circumferential edge 337 and/or adhesive member 338 may enhance the mechanical coupling between the lens capsule and AIOL, thereby increasing the accommodation thereof.

In the dual internal lens system, the effective focal length is adjusted by changing the distance 334 between the lenses 324, 326. For example, the effective focal length, EFL, of the AIOL depicted in FIG. 3C is given as:

$$EFL = \frac{f_1 \times f_2}{f_1 + f_2 - d}, \qquad \text{eq. (3)}$$

where $f_1$ and $f_2$ are the focal lengths of the first and second lenses 324, 326, respectively, and d is the distance 334 therebetween. Accordingly, changing the distance d results in a change of the effective focal length. In some embodiments, either $f_1$ or $f_2$ is negative (i.e., using a diverging lens), resulting in a smaller sum $f_1+f_2$ and giving the distance d a larger influence over the effective focal length. This effect is similar to using a large change of refractive index in the AIOL with a given distance d.

Figure 4:
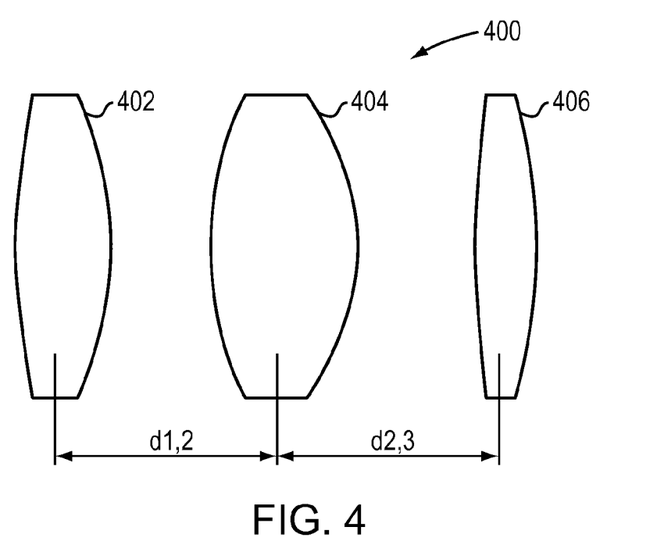
FIG. 4 depicts a three-lens system in accordance with an embodiment of the invention.

Referring to FIG. 4, in some embodiments, the AIOL 400 includes more than two internal optics. The effective focal length is highly influenced by the distances between the lenses. For example, in a three-lens system 400, the effective focal length can be expressed as:

$$EFL = \frac{\left(\frac{f_1 \times f_2}{f_1 + f_2 - d_{1-2}}\right) \times f_3}{\left(\frac{f_1 \times f_2}{f_1 + f_2 - d_{1-2}}\right) + f_3 - d_{2-3}}, \qquad \text{eq. (4)}$$

where $d_{1-2}$ is the distance between lens 402 and lens 404; $d_{2-3}$ is the distance between lens 404 and lens 406; and $f_1$, $f_2$, and $f_3$ are the focal lengths of the lenses 402, 404, 406, respectively. Similar to the two-lens system, the effective focal length of the three-lens system 400 can be tuned by varying the relative distances between the three lenses 402, 404, 406 and the radius of curvature of each lens (which affects the individual focal length). Additionally, the focal length (and therefore the focal power) of the three-lens system 400 can also be adjusted by modifying the refractive index of the medium surrounding the lenses 402, 404, 406 based on equations similar to eqs. (1) and (2). Accordingly, the overall optical power and accommodation of a multiple-lens system is determined by the curvature and refractive index of each lens, the relative positions therebetween, and the refractive index and volume of the filling medium. In addition, when the implanted lens system changes its position in the lens capsule, the overall focusing ability of the eye may change as well.

Figure 5:
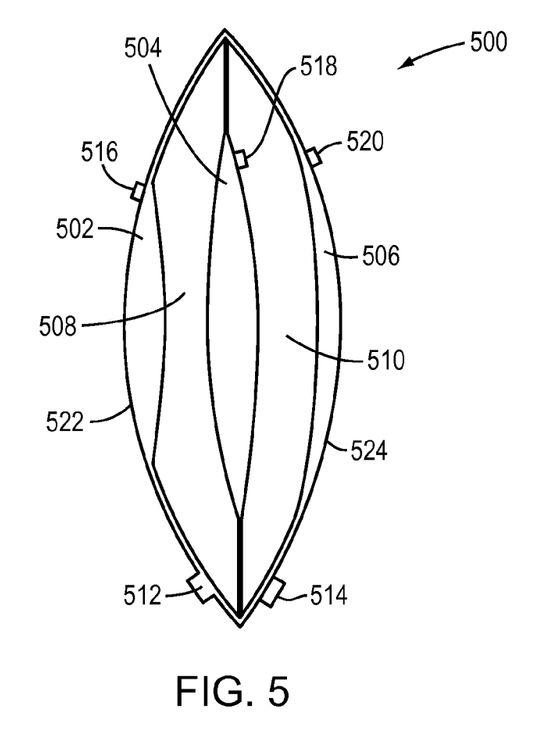
FIG. 5 depicts a three-lens AIOL in accordance with an embodiment of the invention.

Referring to FIG. 5, in various embodiments, the AIOL 500 includes three internal optics: an anterior optic 502, a central optic 504, and a posterior optic 506. An anterior compartment 508 and a posterior compartment 510 located between the optics 502, 504, 506 may be in fluidic connection and filled with the same medium. The filling medium may comprise or consist essentially of one or more of an optical fluid, a gel, a curable polymer, or a compressible fluid (e.g., a gas). In a preferred embodiment, the AIOL 500 is inserted into the eye's lens capsule with the anterior and posterior compartments 508, 510 evacuated; this allows the AIOL 500 to be compressed and/or folded to facilitate implantation through a small surgical incision. After the AIOL 500 is implanted in the lens capsule, the anterior compartment 508 and posterior compartment 510 are filled with a filling medium via a refill valve 512. The volume and components of the filling medium are chosen to optimize the accommodation level and refractive power of the AIOL 500 after implantation. In one embodiment, the anterior compartment 508 and the posterior compartment 510 are not in fluidic connection. The AIOL 500 includes a second refill valve 514 to access the posterior compartment 510 after implantation. Accordingly, the filling volumes of the media in the anterior and posterior compartments 508, 510 may be adjusted individually to optimize the overall accommodation of the AIOL 500 based on the needs of each patient.

Each of the internal optics 502, 504, 506 may be made of a solid material or filled with a fluid (a liquid and/or a gas) that is injected through refill valves 516, 518, 520, respectively. The valves 516, 518, 520 allow the refractive indices of the optics 502, 504, 506 to be adjusted simultaneously or subsequently by changing the filling volume and/or components of the filling fluid(s). The fluid may include or consist essentially of one or more of a flexible polymer, gel, liquid, or compressible fluid to allow the optics 502, 504, 506 to flex during accommodation. The fluid in the optics 502, 504, 506 and the medium filling the anterior and posterior compartments 508, 510 may have the same or different refractive indices and may repel each other to prevent diffusion therebetween. In various embodiments, one or more of the three internal optics 502, 504, 506 are aspheric to minimize optical aberration or designed in a shape to counteract astigmatism. In addition, the internal optics 502, 504, 506 may be deflated or inflated prior to the AIOL implantation into the eye. In various embodiments, the anterior optic 502 and posterior optic 506 are integrated with (i.e., physically part of) the anterior wall 522 and posterior wall 524 of the enclosing IOL, respectively. Again, the thicker portions of the AIOL walls due to the integration of the optics may be used to resist the friction occurring during the AIOL 500 insertion.

Figure 6A:
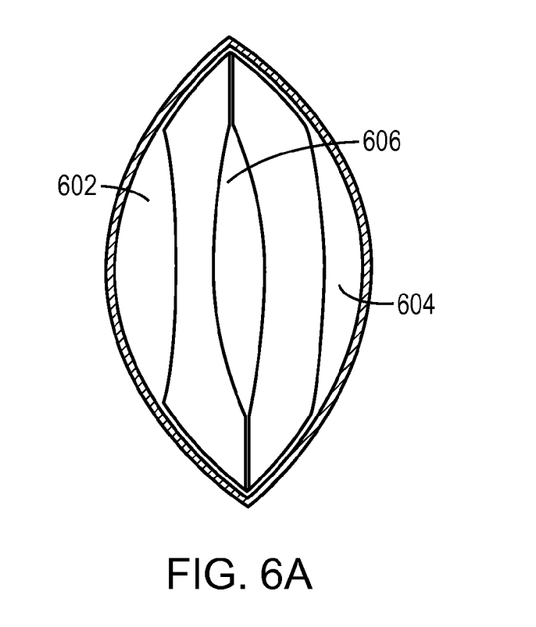
FIGS. 6A and 6B illustrate an AIOL in an accommodated state and in a natural state without accommodation, respectively, after implantation in the lens capsule of an eye in accordance with an embodiment of the invention.
Figure 6B:
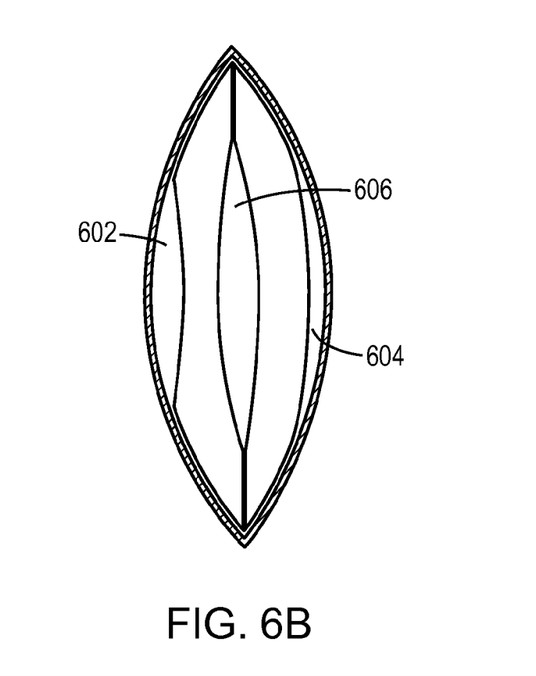

FIGS. 6A and 6B illustrate an operation of the AIOL after implantation in the lens capsule of a patient's eye. Referring to FIG. 6A, during accommodation, the anterior optic 602 and posterior optic 604 move apart (i.e., the distance therebetween increases); as a result, the overall focusing power increases and thus allows light to be focused on an object at a close distance. The curvatures of the anterior and posterior optics 602, 604 may or may not change during accommodation. In another embodiment, the central optic 606 moves preferentially to either the anterior or posterior side of the lens during accommodation. The movements of the optics 602, 604, 606 provide accommodation adjustments. Referring to FIG. 6B, if the AIOL is in a natural state without accommodation, the anterior and posterior optics 602, 604 are closer to each other and less curved; this results in a lower overall optical power of the AIOL.

Figure 7:
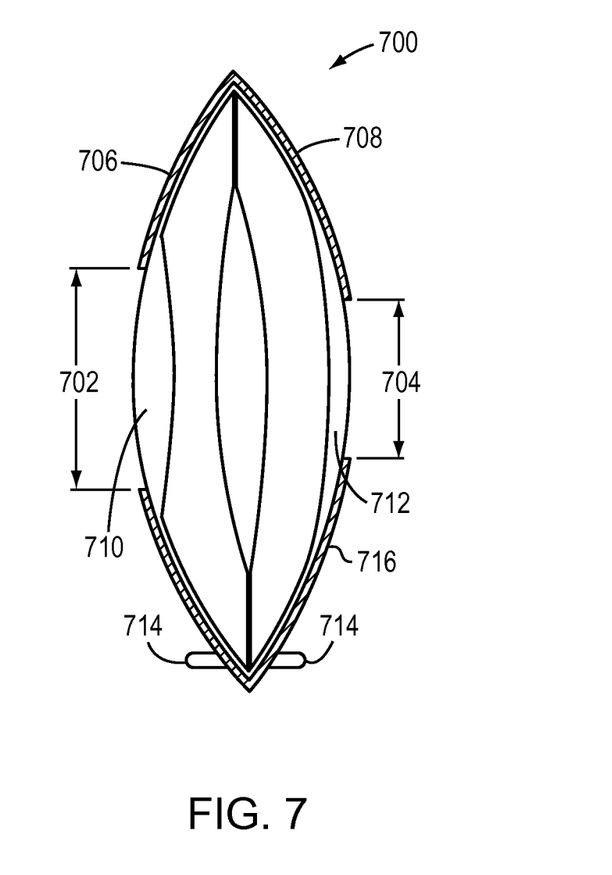
FIG. 7 schematically depicts an AIOL including an anterior capsulotomy and a posterior capsular aperture in accordance with an embodiment of the invention.

Referring to FIG. 7, in some embodiments, the AIOL 700 includes an anterior aperture (i.e., capsular capsulotomy) 702 and a posterior capsular aperture 704 on the anterior wall 706 and posterior wall 708, respectively, to alleviate the ACO and PCO complications. The anterior and/or posterior capsular apertures 702, 704 may be created using, for example, a manual instrument or an Nd:YAG laser. Because the anterior optic 710 and posterior optic 712, placed across the anterior aperture 702 and posterior aperture 704, respectively, are relatively rigid, the optics 710, 712 can support the AIOL 700 during accommodation and relaxation thereof. In various embodiments, the AIOL 700 includes a discontinuous feature (e.g., a groove ring) 714 on the anterior and/or posterior surface to prevent the AIOL 700 from potentially bulging out of the capsular aperture on the lens capsule. The discontinuous feature 714 placed between the AIOL and the surrounding lens capsule may prevent lens epithelial cells from migrating from the lens capsule across to the lens optic. For example, the AIOL may be in contact with the peripheral lens capsule; a groove on the AIOL prevents lens epithelial cells from traveling to the optical center of the AIOL. In one embodiment, the outer surface of the AIOL includes an adhesive layer 716 that mechanically connects the AIOL 700 to the lens capsule; this may prevent the lens epithelial cells from proliferating or migrating as well as enhance the AIOL 700 accommodation. In addition, both anterior and posterior lens capsules may be excised (e.g., each lens capsule may have some material removed therefrom) during the AIOL implantation; this limits the proliferation and migration of the lens epithelial cells along the optical axis of the eye, thereby mitigating post-surgical complications.

The dual-lens or three-lens systems of the AIOL as described above has been shown for illustrative purposes; the present invention is not limited to any particular number of the lenses employed in the implantable AIOL. Any lens systems suitable for use in the AIOLs are within the scope of the present invention.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. An implantable intraocular lens comprising:
   an outer shell comprising at least a first external-access refill valve;
   at least one internal fluid-filled lens including a portion integrated with at least a portion of the outer shell and comprising at least a second external-access refill valve distinct from the first external-access refill valve, the integrated portion of the intraocular lens being thicker and less flexible than, and accommodating differently from, unintegrated portions of the intraocular lens; and
   a first fluid at least partially filling the outer shell,
   wherein a refractive index of the first fluid, a degree of filling of the outer shell with the first fluid, a curvature of the outer shell, an axial position of the at least one internal fluid-filled lens, and a curvature of the at least one internal fluid-filled lens cooperate to define an accommodation and a refractive power of the intraocular lens.

2. The implantable intraocular lens of claim 1, wherein the at least one internal fluid-filled lens is made of a curable material.

3. The implantable intraocular lens of claim 1, wherein, the at least one internal fluid-filled lens is a diverging lens.

4. The implantable intraocular lens of claim 1, wherein the at least one internal fluid-filled lens comprises a second shell at least partially filled with a second fluid, the first and second fluids exhibiting mutual repulsion therebetween.

5. The implantable intraocular lens of claim 4, wherein the second external-access refill valve allows selective passage therethrough of the second fluid.

6. The implantable intraocular lens of claim 5, wherein the first and second fluids have different refractive indices.

7. The implantable intraocular lens of claim 1, wherein the at least first external-access refill valve allows selective passage therethrough of the first fluid.

8. The implantable intraocular lens of claim 1, wherein a refractive index of the first fluid is different from that of an aqueous humor in an eye.

9. The implantable intraocular lens of claim 1, wherein an outer surface of the outer shell comprises a feature creating a discontinuity thereon.

10. The implantable intraocular lens of claim 1, wherein an outer surface of the outer shell comprises an adhesive.

11. The implantable intraocular lens of claim 1, wherein an outer surface of the outer shell is modified with functional groups to prevent proliferation or migration of lens epithelial cells.

12. The implantable intraocular lens of claim 1, wherein the first fluid is a pharmacological agent.

13. The implantable intraocular lens of claim 1, wherein the at least one internal fluid-filled lens consists of two optics, the optics being integrated with opposed inner surfaces of the outer shell whereby a change in relative position between the optics alters the accommodation.

14. The implantable intraocular lens of claim 1, wherein the outer shell is shaped to conform to a geometry of an eye.

15. The implantable intraocular lens of claim 1, wherein at least one of the outer shell, the at least one internal fluid-filled lens, or the first fluid comprises at least one blue-light-absorbing chromophore.

16. The implantable intraocular lens of claim 1, wherein the accommodation and refractive power of the intraocular lens is further defined by a degree of filling of the at least one internal fluid-filled lens.

17. The implantable intraocular lens of claim 1, wherein the at least one internal fluid-filled lens is integrated with an anterior surface of the outer shell.

18. The implantable intraocular lens of claim 17, further comprising a second internal fluid-filled lens including a second portion integrated with at least a portion of a posterior surface of the Outer shell and comprising at least a third external-access refill valve, the second integrated portion of the intraocular lens being thicker and less flexible than, and accommodating differently from, unintegrated portions of the intraocular lens.

* * * * *